United States Patent [19]

Mahe et al.

[11] Patent Number: 5,061,448

[45] Date of Patent: Oct. 29, 1991

[54] INCUBATOR

[75] Inventors: Stanley R. Mahe; William R. Biver, both of Dubuque, Iowa

[73] Assignee: Barnstead Thermolyne Corporation, Dubuque, Iowa

[21] Appl. No.: 187,815

[22] Filed: Apr. 29, 1988

[51] Int. Cl.$^5$ .............................................. B01L 7/00
[52] U.S. Cl. .................................... 422/99; 422/104; 422/307; 435/284; 435/290; 435/299; 435/300; 435/809; 34/52; 34/54; 34/105; 34/164; 34/179; 34/180; 34/181; 34/187; 34/210; 34/212

[58] Field of Search ......................... 422/99, 104, 307; 435/284, 287, 290, 299, 300, 809; 34/52, 54, 105, 164, 179-181, 187, 210, 212

[56] References Cited

U.S. PATENT DOCUMENTS

| | | | |
|---|---|---|---|
| 3,002,895 | 10/1961 | Freedman | 435/360 |
| 3,535,208 | 10/1970 | Sasaki et al. | 435/287 |
| 3,618,734 | 11/1971 | Khan | 34/219 |
| 3,634,651 | 1/1972 | Siegal et al. | 219/400 |
| 3,832,532 | 8/1974 | Proglin et al. | 364/413.01 |
| 4,356,967 | 11/1982 | Lunick | 422/104 X |
| 4,572,427 | 2/1986 | Selfridge et al. | 236/3 |
| 4,689,303 | 8/1987 | Kraft et al. | 435/290 |

FOREIGN PATENT DOCUMENTS 1112919  5/1968  United Kingdom .

OTHER PUBLICATIONS

Sales Literature; Lab-Line Orbit Incubator Shaker; Model 3528 & Model 3593.
Sales Literature of New Brunswick Scientific Incubator Shakers; Models G25-KC/G25-KLC & G24.

Primary Examiner—Robert J. Warden
Assistant Examiner—Lynn M. Kummert
Attorney, Agent, or Firm—Marjama & Pincelli

[57] ABSTRACT

An apparatus for incubating and/or incubating shaking biological test specimens having a detachable autoclavable chamber. The main incubating chamber is provided with a support plate and diffuser plate for directing a controlled flow of heated air to the biological test specimen. A transverse blower is provided to assist in providing uniform air flow within the main incubating chamber.

5 Claims, 9 Drawing Sheets

INCUBATOR

BACKGROUND OF THE INVENTION

The present invention relates to incubators and incubator shakers for maintaining cells, microrganisms and other biological test samples in a controlled environment.

A problem with prior art incubators and incubator shakers are their ability to provide a uniform and tightly controlled temperature within the incubating chamber. In certain laboratory tests, for example, such as the enzyme immunoassy test for the AIDS virus, it is necessary to keep a set temperature within the chamber in a temperature range generally from about 37° C. to 56° C. It is important that the temperature not deviate more than $\pm \frac{1}{2}$° C. In this type test, it is extremely important that the temperature throughout the incubator chamber be substantially uniform. It is also important that the operating temperature be reached in a quick, uniform and efficient manner. Typically, such tests have been conducted in a waterbath incubation device. However, waterbaths have the disadvantage of cross contamination exposure and an exposure risk to the technologist performing the test. Substitutes, such as an aerobic incubator for waterbath have been tried, however they have not been able to offer the uniform rapid heatup as compared to a waterbath. Another problem associated with prior art incubators is the ability to clean and disinfect the incubating chamber. For example, when a positive test result is found for the AIDS virus, it is important that the chamber be thoroughly disinfected and/or sterilized. Prior art devices have been limited to hand cleaning. Another important aspect in carrying out tests with contagious diseases is that the test specimens do not contaminate other test specimens. It is therefore important that the air flow within the incubating chamber be carefully controlled to minimize any potential cross contamination.

Applicants have invented a new and improved incubator and incubator shaker wherein a very uniform and constant temperature can be maintained while minimizing or eliminating the problems of the prior art.

SUMMARY OF THE INVENTION

In one aspect of the present invention, there is provided an apparatus for incubating a biological test specimen. The apparatus includes a base support section, a removable incubating chamber and a blower drive means detachably mounted to the incubating chamber.

In another aspect of the present invention, there is provided an apparatus for incubating a biological test sample having a main incubating chamber. A support plate is provided therein for supporting test specimens. The support plate has a plurality of openings, one associated with each test specimen. A diffuser plate is provided between the support plate and the bottom of said incubating chamber so as to provide a pressure staging area between the support plate and diffuser plate and an air receiving area between the diffuser plate and bottom of the incubating chamber.

In yet another aspect of the present invention, there is provided an apparatus for incubating a test specimen wherein blower means are provided which extend at least 50% of the width of the incubating chamber.

DETAILED DESCRIPTION

Figure 1:
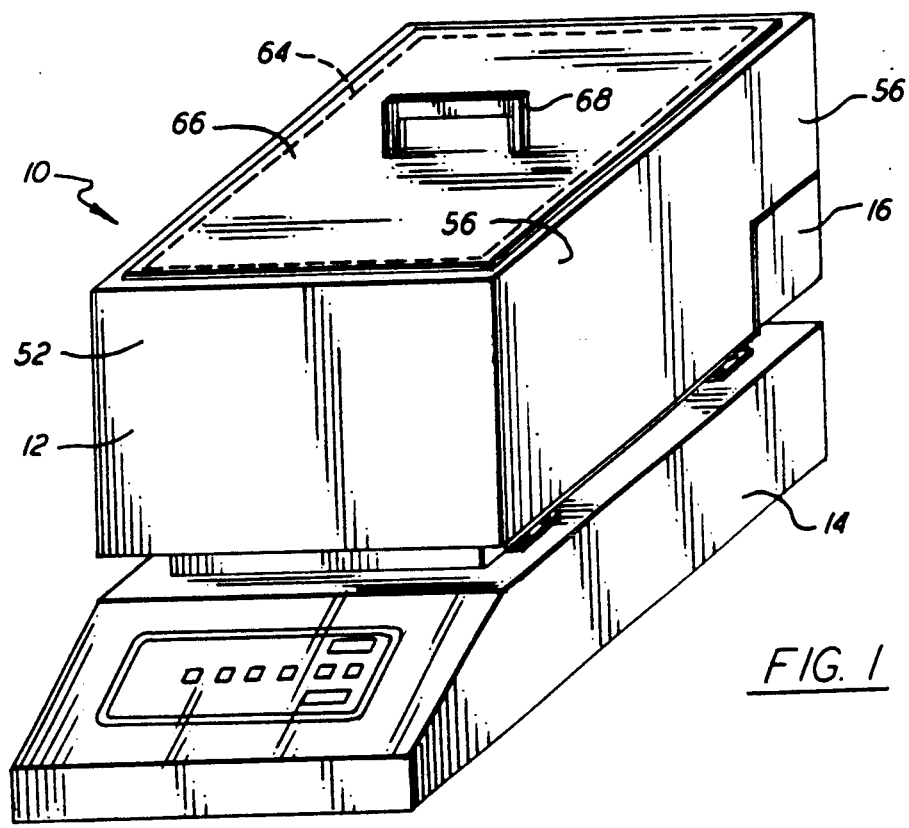
FIG. 1 is a front perspective view of an apparatus made in accordance with the present invention.
Figure 1A:
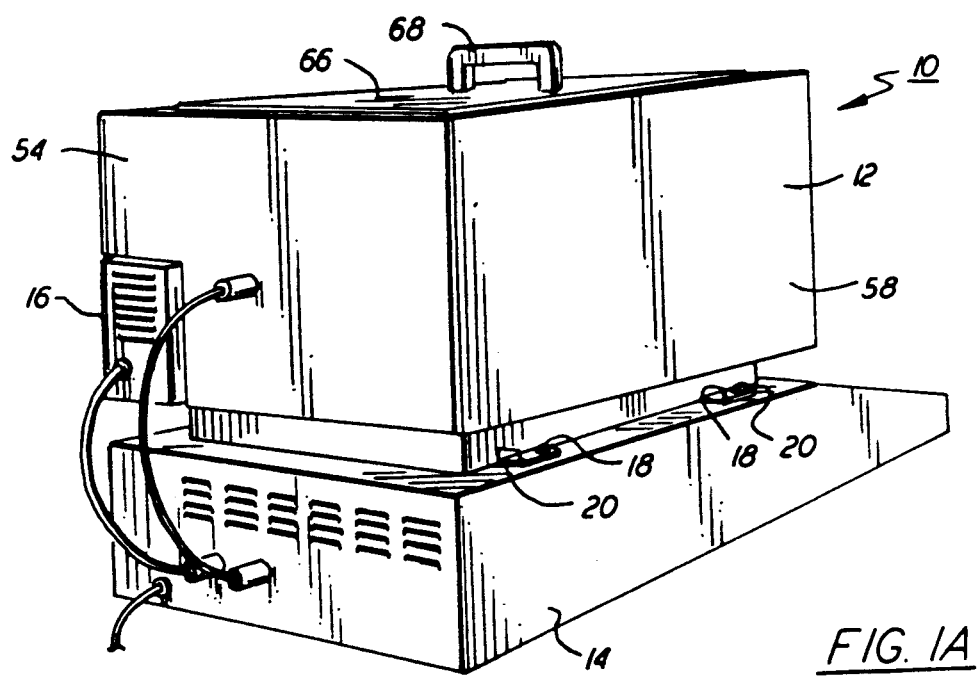
FIG. 1A is back perspective view of the apparatus of FIG. 1.
Figure 2:
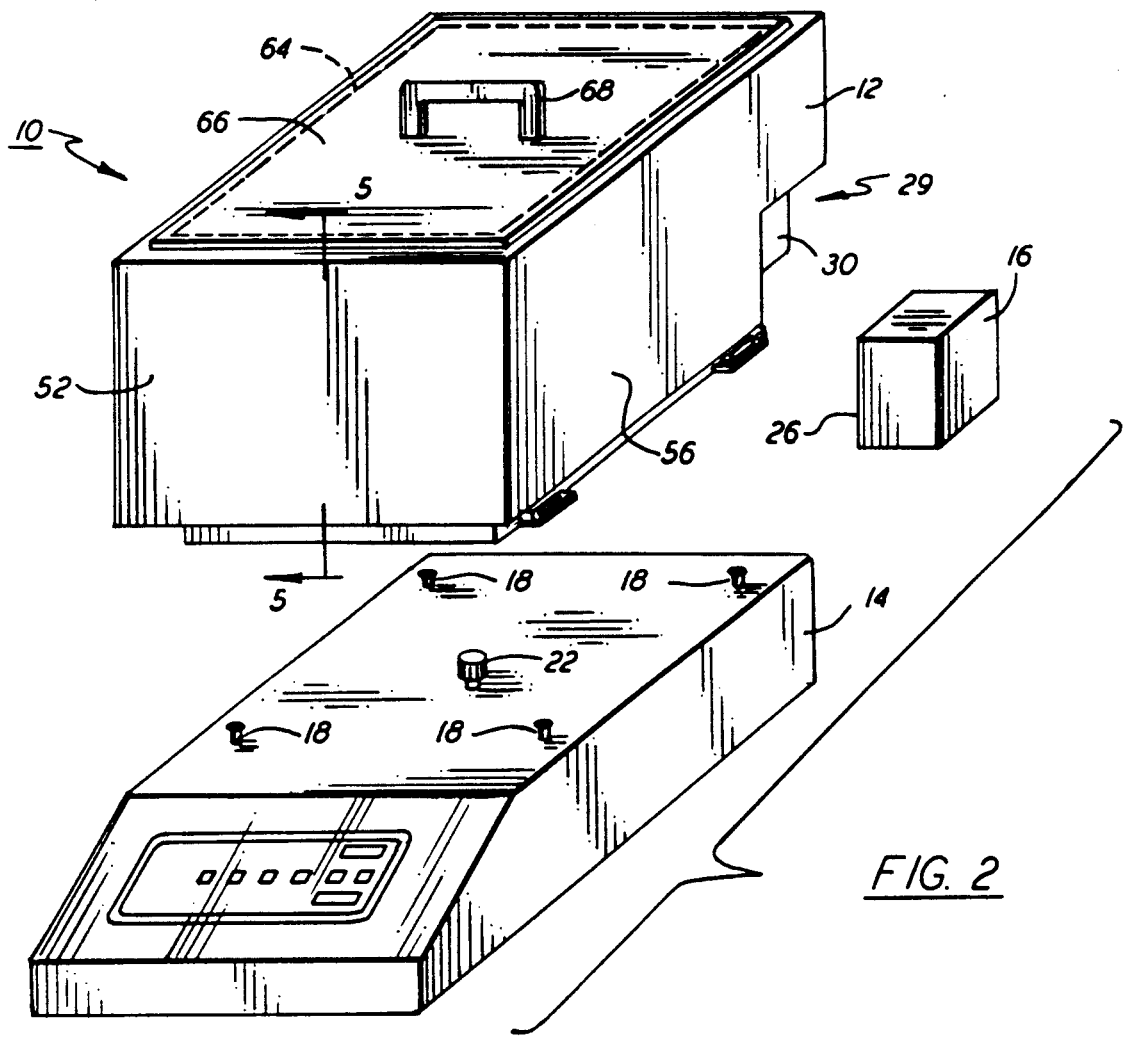
FIG. 2 is a perspective view of a portion of the apparatus of FIG. 1.
Figure 2A:
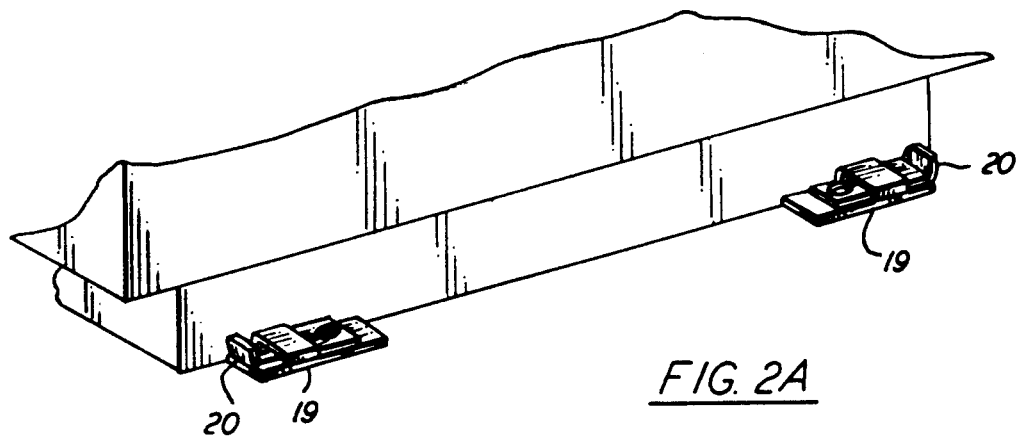
FIG. 2A is a fragmenting view of the bottom of incubating chamber assembly.
Figure 4:
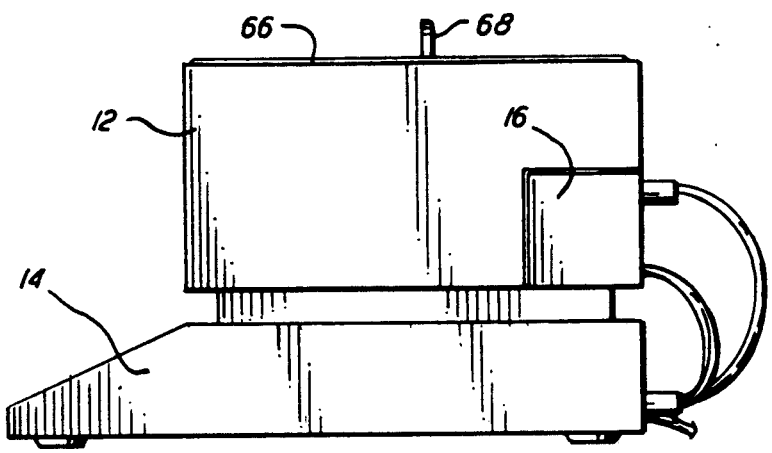
FIG. 4 is a side elevation view of the apparatus of FIG. 1.

Referring to FIGS. 1-4, there is illustrated an apparatus 10 made in accordance with the present invention. The apparatus 10 may take the form of an incubator or an incubator shaker. The apparatus 10 comprises three separate components; a base section 14, an incubating chamber assembly 12 which is detachably mounted to base section 14 and a blower drive assembly 16 detachably mounted to the incubating chamber assembly 12. The incubating chamber assembly 12 has a plurality of mounting pins 18 for placement within receiving latches 20 mounted to mounting flange 19 of incubator chamber assembly 12. (See FIG. 2A). The mounting pins 18 and corresponding receiving latches 20 are designed to firmly secure the incubating chamber assembly 12 to base section 14. It is to be understood that various other means may be used for detachably mounting the incubator chamber assembly 12 to base section 14.

The base section 14 houses the control means for determining the temperature of incubation and various other controlled functions as is typically done in prior art devices. Appropriate sensors are connected by appropriate detachable cables between the base section 14 and incubator chamber assembly 12. The base section 14 also houses an agitating motor therein which has an output drive shaft 22 capable of being connected to a connecting drive shaft 92 in incubating chamber assembly 12 which is discussed in more detail later herein.

Figure 11:
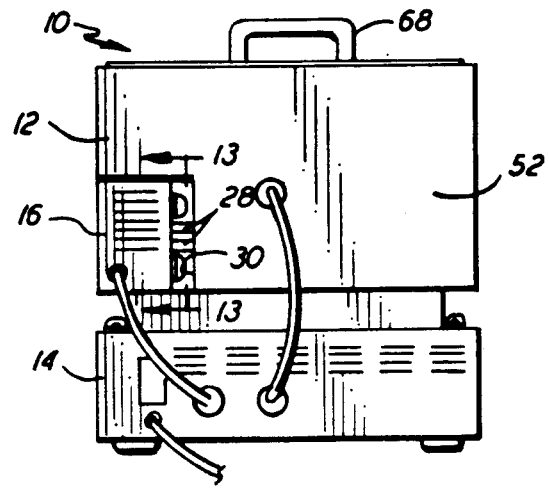
FIG. 11 is back plan view of the apparatus of FIG. 1.
Figure 13:
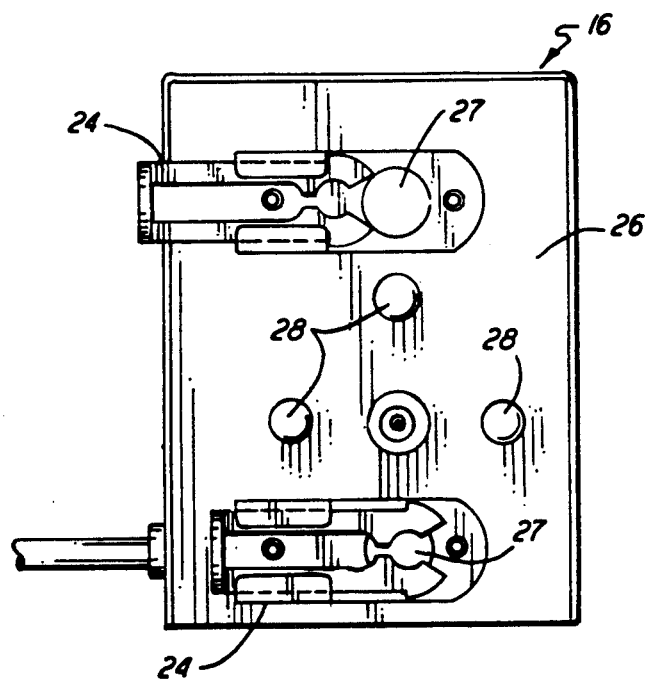
FIG. 13 is a front plan view of the blower drive assembly as taken along line 13—13 of FIG. 11.
Figure 12:
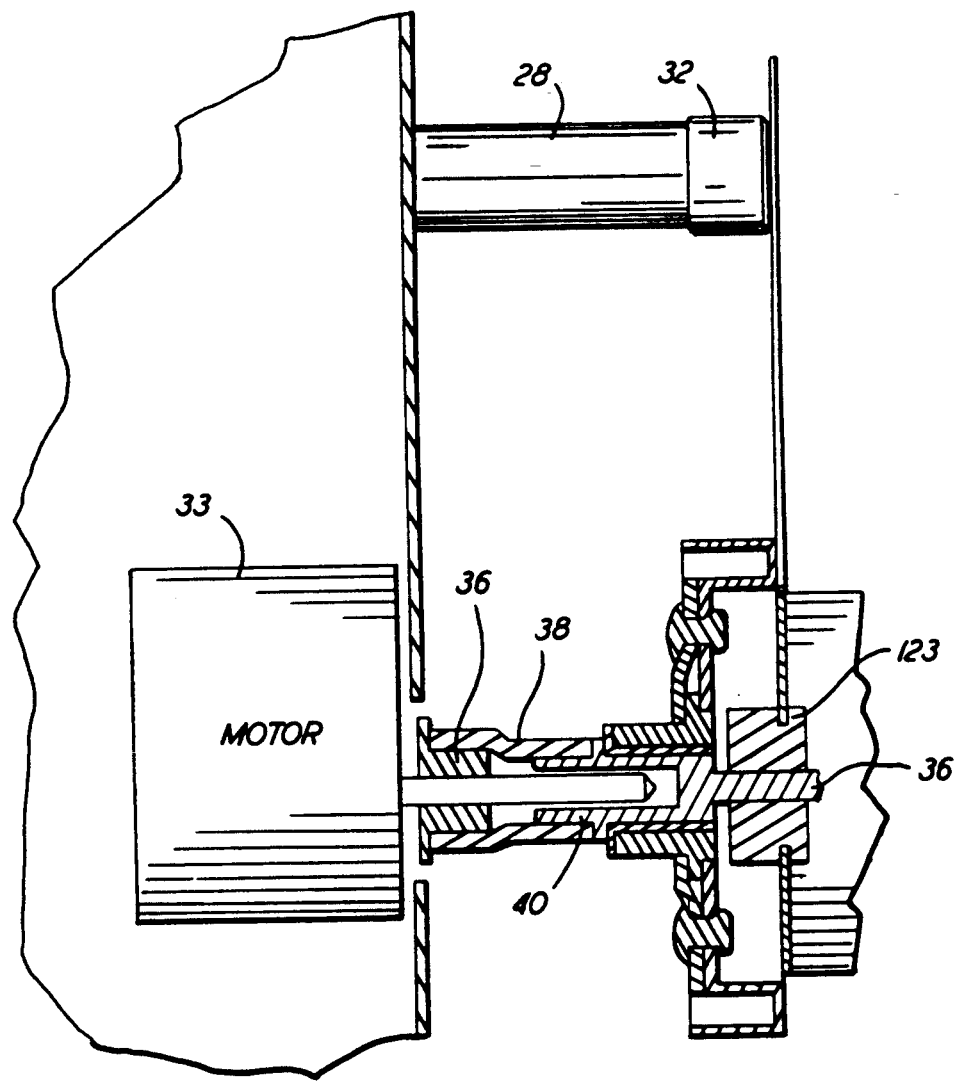
FIG. 12 is an enlarged cross-sectional partial view illustrating the connection of the blower drive assembly to the incubating chamber.

Referring to FIGS. 11, 12 and 13, the blower drive assembly 16 is shown in greater detail. The blower drive assembly 16 is provided with a pair of slidable mounting clips 24 secured to the mounting face 26 of drive assembly 16. The slidable mounting clips 24 are designed to engage a pair of aligned mounting pins 28 secured to chamber assembly 12 The pins 28 enter an opening 27 in its corresponding clip 24 and when the clips 24 are pushed in, the clips 24 engage and clamp pins 26 so as to firmly secure the blower drive assembly 16 to the chamber assembly 12. Likewise, when the clips 24 are pulled out, they release the pins 26 to allow removal of blower drive assembly 16. In the present invention, the chamber assembly 12 and blower drive means 16 are shaped such that when they are attached, they form a generally smooth outer configuration. In the present invention, this is accomplished by providing chamber assembly 12 with a recess area 29 which has a configuration which corresponds to the outer configuration of the blower drive assembly 16. It is, of course, understood that the mounting means for securing the blower drive means 16 to incubator chamber assembly 12 may take any form desired and the outer configuration need not be smooth.

Referring to FIG. 12, there is illustrated an enlarged cross sectional view of the blower drive assembly 16 mounted to incubator chamber assembly 12. The blower drive assembly 16 has three mounting spacers 28 (see FIG. 13) which maintain blower drive assembly 16 a predetermined distance from mounting face 30 of incubating chamber assembly 12. Preferably, as illustrated, mounting spacers 28 are provided with rubber cushion means 32 for absorbing the vibrations between blower drive assembly 16 and incubating chamber assembly 12.

The blower drive assembly 16 has a blower drive motor 33 mounted therein which turns a drive bushing 36. A flexible cylindrical drive coupling 38 is provided and is secured to bushing 36 by simply pressing one end over the drive bushing 36. The other end of the flexible cylindrical drive coupling 38 is connected to the drive shaft 40 of blower assembly 40 mounted within incubating chamber assembly 12. Flexible coupling 38 provides a simple but reliable means for accounting for any misalignment between drive shaft 40 and drive bushing 36. This avoids the necessity of providing an expensive alignment feature.

Figure 5:
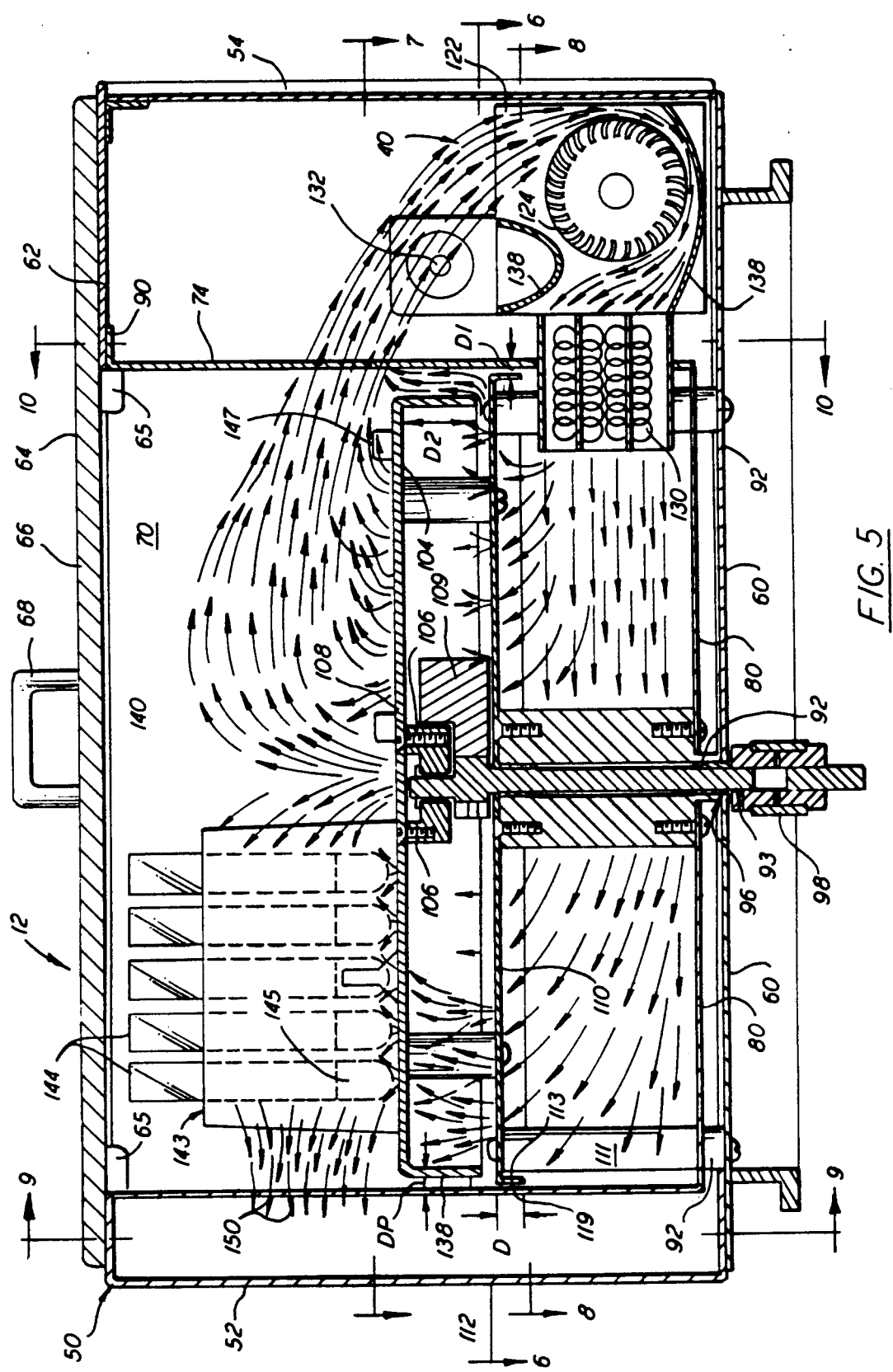
FIG. 5 is a cross-sectional view of the incubating chamber of the apparatus of the present invention as taken along the line 5—5 of FIG. 2.
Figure 7:
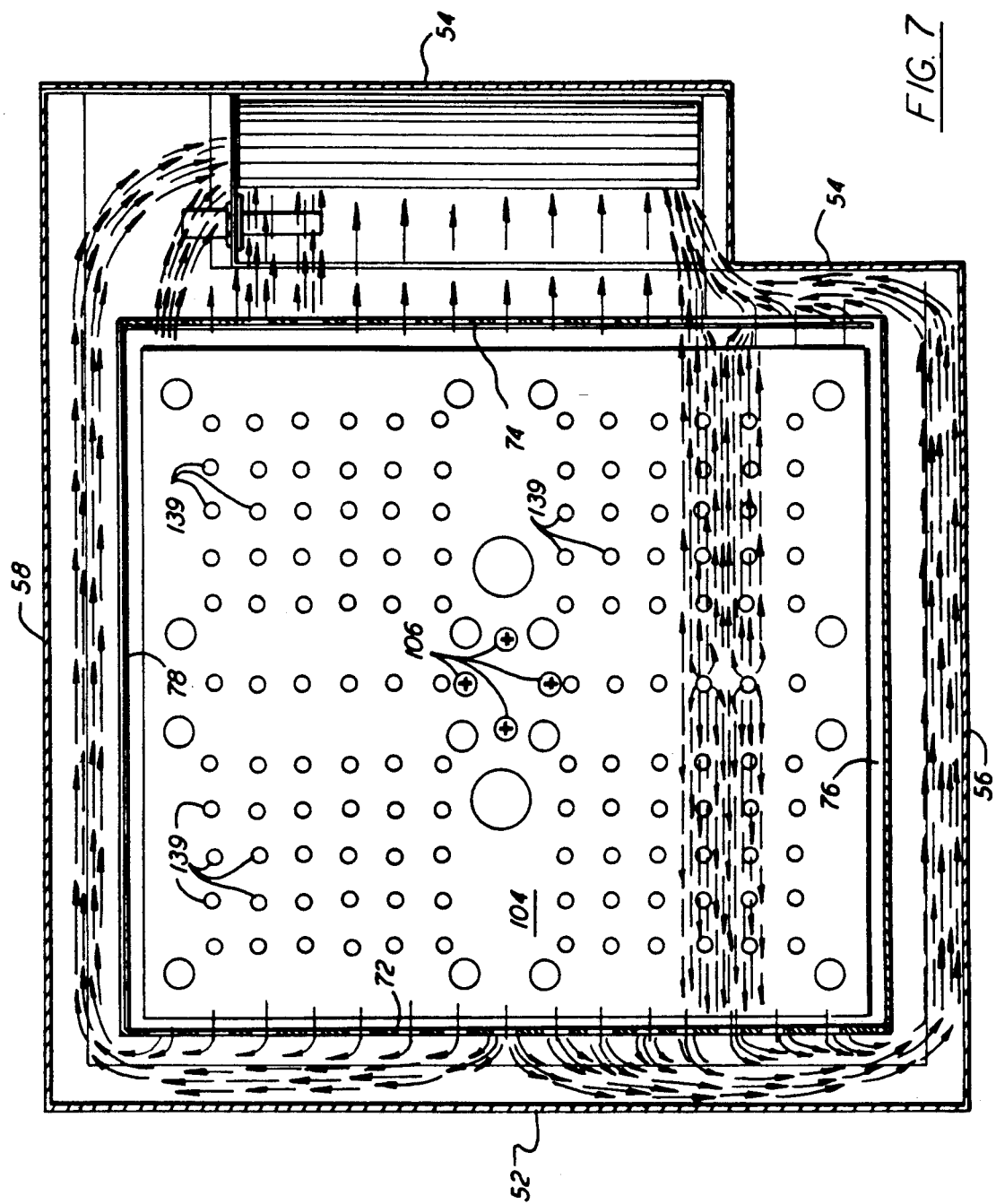
FIG. 7 is a cross-sectional view of the incubating chamber illustrating the shaker plate taken along line 7—7 of FIG. 5.

Referring to FIGS. 5 and 7, there is illustrated cross-sectional views of incubator chamber assembly 12. The incubator chamber assembly 12 comprises a housing 50 having a front wall 52, back wall 54, right side wall 56, left side wall 58, bottom wall 60 and top wall 62. The top wall 62 is provided with an access opening 64 for placement of biological test specimens within the incubator chamber assembly 12. A removable top cover 66 is provided for placement over access opening 64. Top cover 66 is provided with four (4) spacers 65 on the bottom surface for aligning top cover 66 with opening 64. In the particular embodiment illustrated, top cover 66 is provided with a handle 68 for lifting the top cover off access opening 64. Provided within housing 50 is an inner main chamber 70 which comprises a front wall 72, back wall 74, right side wall 76 and left side wall 78 and bottom wall 80 which connects the front wall 72 back wall 74 right side wall 76 and left side wall 78. The walls 72, 74, 76, and 78 are each provided with a flange 90 located at their up end. The flanges 90 are placed adjacent top wall 62, preferably a silicone rubber layer is placed between flanges 90 and top wall 62. The bottom surface 80 is supported by spacers 92 which are secured to the bottom wall 60 of housing 50.

Mounted substantially centrally in the inner main chamber 70 is offset shaft 92. Shaft 92 is mounted such that it can rotate about its axis. The offset shaft 92 has a lower end 93 which extends through an opening 96 in the bottom wall 60. Lower end 93 engages a coupling 98 which is connected to output drive shaft 22 in base section 14. The upper end of the shaft 92 is provided with a counterweight 109 to compensate for the off center rotation. Secured to the upper end 102 of shaft 92 is a bearing and bearing holder (not shown) attached to support plate 104. In the particular embodiment illustrated, the bearing holder is attached to the offset shaft 92 by a retaining clip (not shown) and the support plate 104 is secured to the bearing holder with four (4) screws 106 which pass through openings 108 in support plate 104. While screws have been shown to secure the support plate 104 to the shaft 92 any other desired means may be used to secure support plate 104 to shaft 92. Plate 104 has an outer peripheral edge 117. The plate 104 is designed such that the peripheral edge 117 is as close to walls 72, 74, 76 and 78 as possible. However, due to its orbital rotation, plate 104 will vary in distance from walls 72, 74,76 and 78. Preferably, plate 104 is designed such that peripheral edge 117, at its closest point to walls 72, 74, 76 and 78, is spaced a distance DP of about 1/16 inch.

Figure 6:
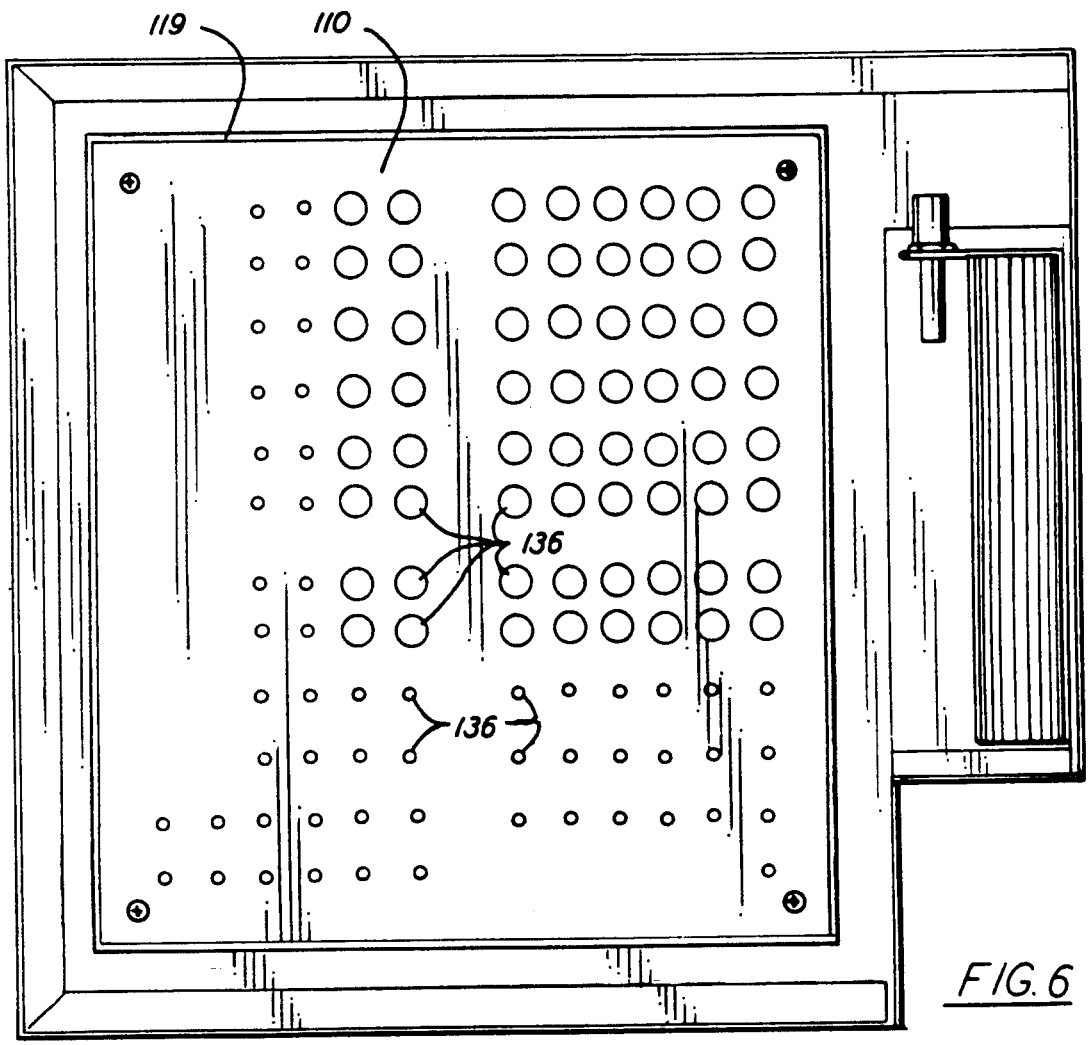
FIG. 6 is a cross-sectional view of the incubating chamber illustrating the diffuser plate mounted in the incubating chamber as taken along line 6—6 of FIG. 5.

Referring to FIGS. 5 and 6, a diffuser plate 110 is provided within main chamber 70 and extends substantially across the cross-sectional area of main chamber 70 as illustrated in FIGS. 5 and 6 so as to provide a receiving area 115 between bottom wall 80 and diffuser plate 110. The diffuser plate 110 may be secured to the housing in a desired manner. In the particular embodiment illustrated, diffuser plate 110 is secured to spacers 111 by screws 112 and the spacers 111 are secured to spacers 92 which are secured to bottom wall 80. The diffuser plate 110 has an outer peripheral skirt 113 which extends downward a distance D. Applicants have found that skirt 113 should extend a distance D of at least ¼ inch and preferably of at least one inch. Diffuser plate 110 is provided with a plurality of openings 136 which are sized and located so as to provide a substantial uniform pressure area between the diffuser plate and bottom of support plate 104. Skirt 138 has a downward extending skirt 104 which extends a distance D2, preferably, D2 is at least ½ inch. In the particular embodiment illustrated, the skirt 138 extends down a distance D2 of about ¾ inch.

The particular size and location of opening 136 was arrived at by trying various size and location combinations until the desired pressure distribution was obtained. As illustrated in FIG. 6, the upper right portion of diffuser plate 110 is provided with larger opening and in some places, no openings are provided. As with support plate 104, the peripheral edge 119 is spaced as closely as possible to walls 72, 74, 76 and 78. In the particular embodiment illustrated, peripheral edge 119 is spaced a distance D1 of about 1/16 of an inch.

Figure 8A:
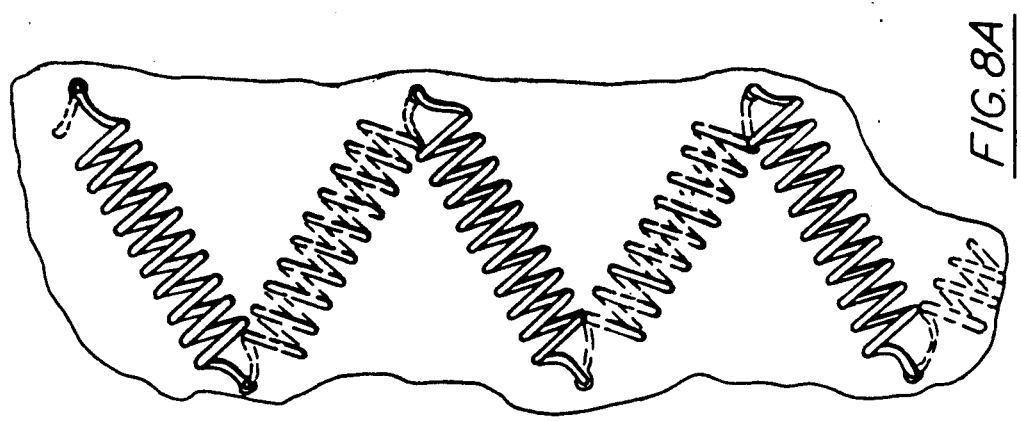
FIG. 8A is an enlarged view of the heating element of the heater as shown by the circle in FIG. 8.
Figure 8:
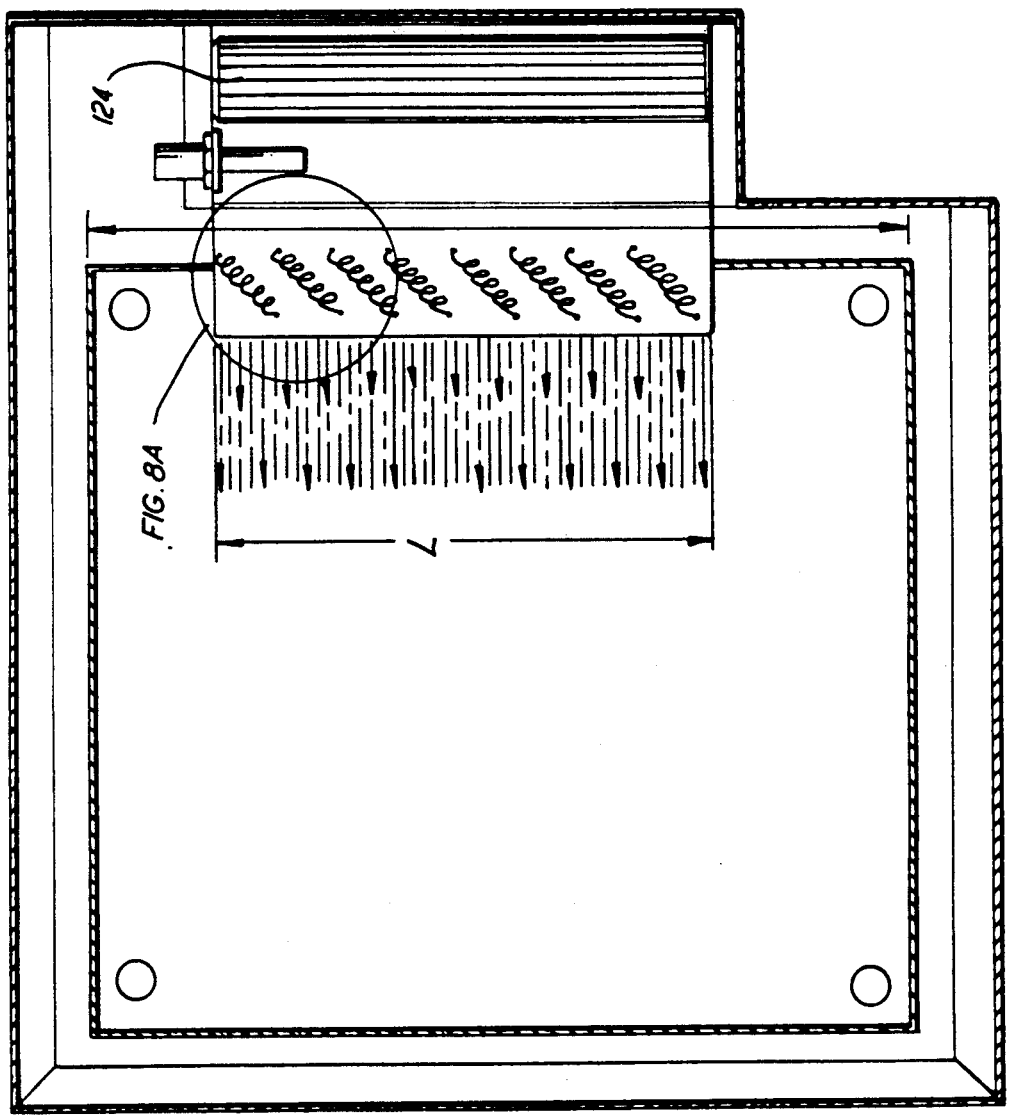
FIG. 8 is a cross-sectional view of the incubating chamber of FIG. 5 taken along the line 8—8 illustrating the air receiving area.
Figure 9:
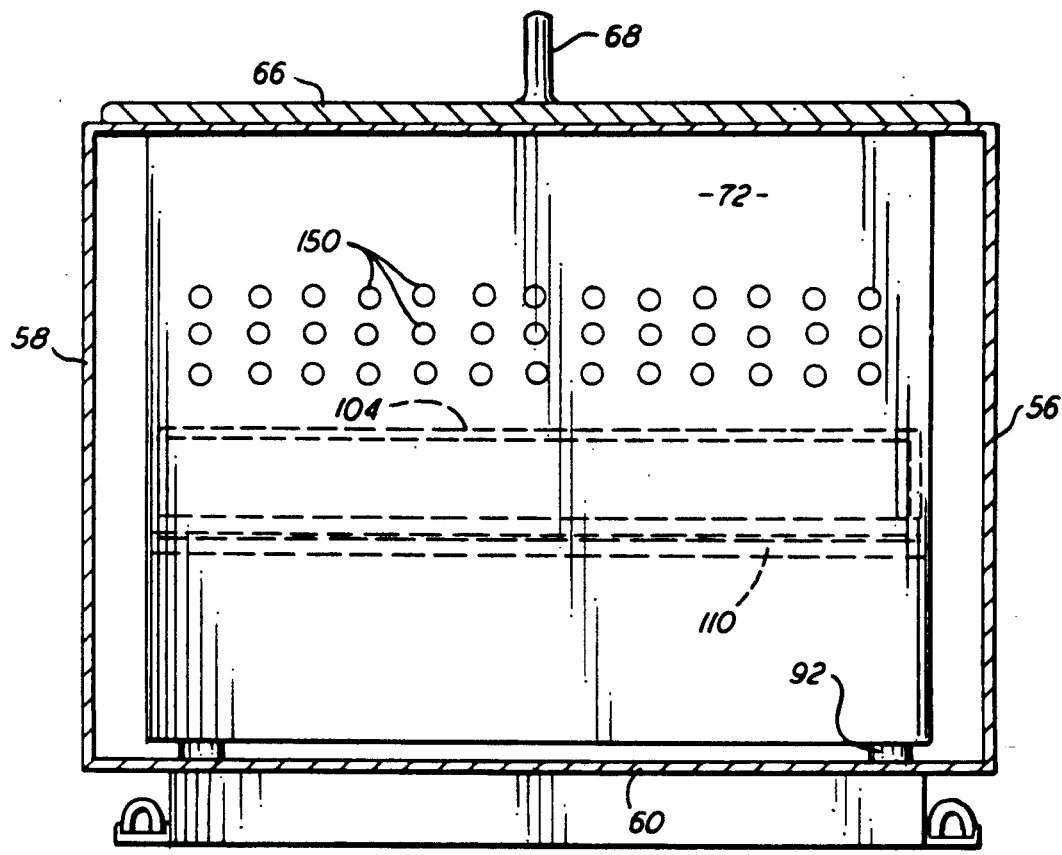
FIG. 9 is a side cross-sectional view of the incubating chamber of FIG. 5 taken along line 9—9.
Figure 10:
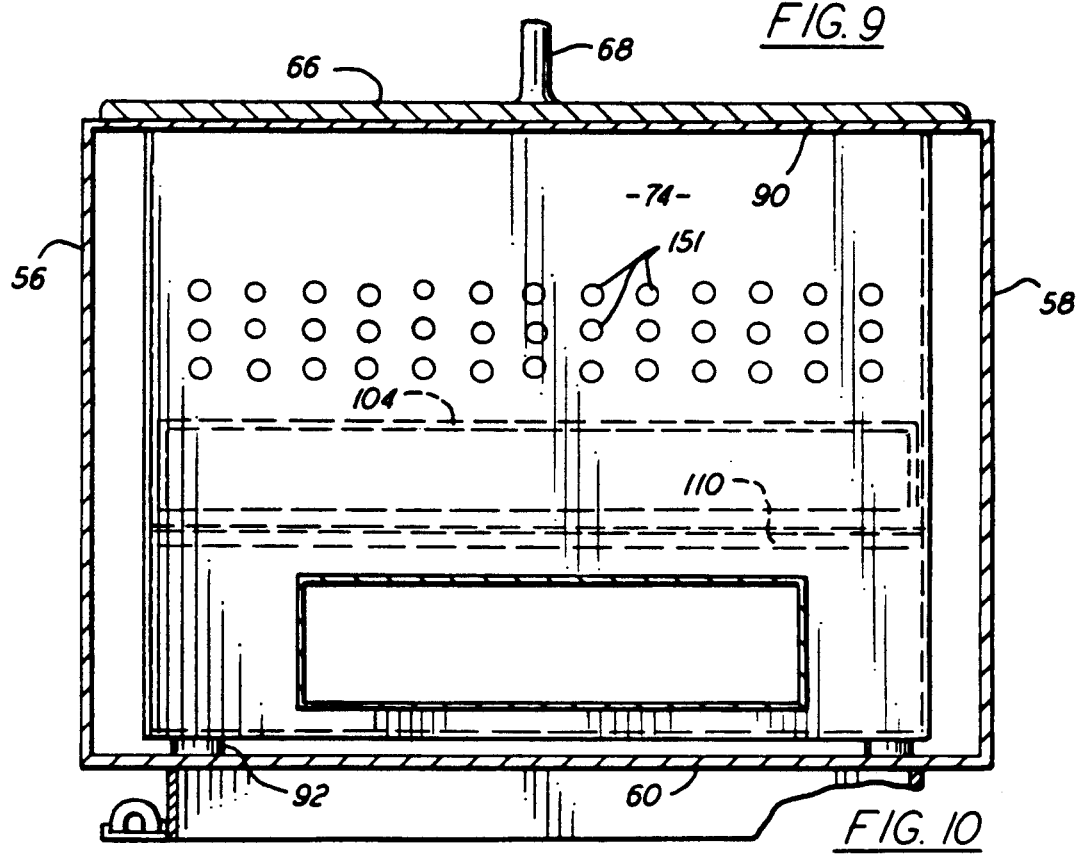
FIG. 10 is a side cross-sectional view of the incubating chamber of FIG. 5 taken along line 10—10.
Figure 3:
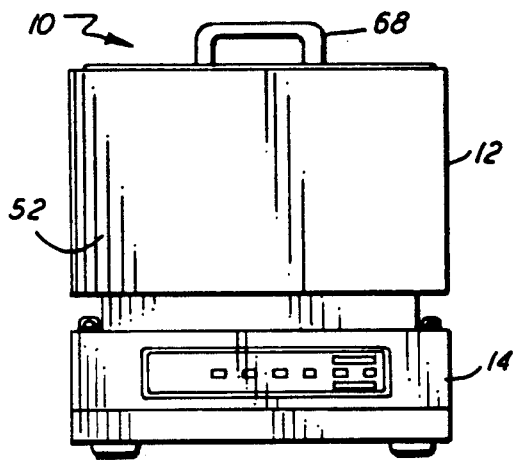
FIG. 3 is a front elevation view of the apparatus of FIG. 1.

A blower assembly 40 is provided within incubating chamber assembly 12 and is located such that its output is in direct communication with the receiving area 15 between the diffuser plate 110 and the bottom wall 80 of the inner chamber 70. The blower assembly 40 includes a housing 122 which contains a squirrel cage type impeller 124 which is mounted to side rails 126 of housing 122 by bushings assembly 123. The impeller 24 is designed to receive air through openings in the top of the housing 122 and direct air out the side wall 128 through outlet port 129 into the receiving area 115 of inner main chamber 70. Placed at the exit of the blower assembly 40 is heating means which heats the air entering inner chamber 70 to the preselected temperature. In the particular embodiment illustrated, heating means comprise heating coils 130 arranged in a zig-zag pattern (See FIGS. 8 and 8A) which are made of an autoclavable material. The elements or coils 130 extend substantially across the entire length of outlet port 129.

Baffles 130 are provided for appropriately directing the air flow from the impeller 124 into inner chamber 70. The impeller 124 is designed to extend substantially across the width W of the chamber 70. The outlet port 129 of blower assembly 120 has a length L which is at least 30% of the width W of the inner chamber 70. Preferably, the length L of outlet port 129 is at least 50% of the width W of the chamber 70. In the particular embodiment illustrated the length L is approximately 60% of W. This helps assure more uniform airflow and pressure distribution within the receiving area 115. The heating elements 130 are controlled by a solid state temperature controller as is well known in the art in response to a temperature sensor 132 disposed on the top of blower assembly 40. In the particular embodiment illustrated, the impeller 124 is designed to provide an air flow of approximately 36 cfm. The air which enters the receiving area 115 is forced upward through openings 136 in diffuser plate 110. The openings 136 having a size and are located so as to provide a substantial uniform pressure between the diffuser plate 110 and the bottom of the support 104. The skirt 138 helps provide a staging area for the air coming through the diffuser plate 110 prior to entering the main incubation area 140 above the support plate 104.

Support plate 104 is provided with a plurality of openings 139, each opening 139 is designed to be associated with a biological test specimen. As can be seen in FIGS. 5 and 7, there are provided two test tube racks 143 each having the plurality of test tubes 144 therein. Each test tube 144 has therein a biological test specimen 145 to be exposed to the incubation environment. The test tube racks 143 are positioned by a plurality of spacers 147 that are designed to mate with the test tube racks 143 so as to hold them firmly in position. Each test tube rack 143 has an appropriate matrix for holding a desired number of test tubes 144. The support plate 104 is designed such that one opening 139 is associated with each test tube and is located substantially below where the specimen is placed.

The front wall 72 is provided with a plurality of openings 150 which are located above the support plate 104 and below the top of the test tubes 144. Air is drawn through openings 150 between sides of the housing and inner chamber to the blower assembly 40. Back wall 74 is also provided with a plurality of openings which are disposed above the support plate 104 below the top of the test tubes. Applicants have found that it is important to avoid air flow around the top of the test tubes 104 (or other type container) as this can cause siphoning or cross-contamination of the biological test specimens between test tubes 144.

A brief description of the operation of the apparatus 10 according to present invention will now be discussed. The top cover 66 is removed to allow access within the inner chamber 70. A plurality of test tube racks 143 (typically 2 or 4) are placed in inner chamber 70, each test tube having test tubes 144 with biological specimens therein. Test tube rack 143 is designed for mating with the support plate 104. After the racks 143 have been properly secured to support plate 104, the top cover is placed on the incubator/shaker. The appropriate test conditions are set into the apparatus as is commonly done in the prior art. Thereafter, the heater and blower assembly are turned on to provide circulation of heated air to chamber 70. The arrows illustrate the air flow that takes place. Sensors 132 monitor the temperature within chamber 70 and for controlling the amount of heat to be applied by the heating elements. Air flows into the receiving area from the blower assembly 40 at a relatively high rate of velocity. The openings in the diffuser plate 110 direct the air toward the support plate 104 in a manner such that the pressure above the diffuser plate 110 is substantially uniform. The openings 136 in support plate 104 are distributed directly below each specimen. The air then flows around the bottom test tubes 144 and out the front or back walls 72, 74 through the appropriate openings therein. As can be seen, the air going out the front wall 72 will go through side passages back to the blower assembly 40. This type of air movement provides for quick heating of the incubation inner chamber to its operating temperature and allows for efficient exchange of heat to the temperature sensor 132 to provide extremely constant temperature control.

As previously discussed, the support plate 104 of the present invention is designed for orbital movement as is well known in the art of incubator shakers. Thus, at the appropriate time, the apparatus activates the drive motor in base section 16, this causing the shaker plate 104 to shake its pre-designed motion.

Applicants have found that an apparatus made in accordance with the present invention, bringing the temperatures to the operating range within about 6 to 10 minutes and that the temperature can be maintained within $\frac{1}{4}°$ centigrade uniformly throughout the entire chamber 70.

After the operating cycle has been completed, the test specimens are removed from the chamber 70 and the chamber 70 is appropriately cleaned down by the appropriate method. In certain instances, it is desirable that the incubating chamber be thoroughly cleaned. Typically, in the prior art, this is accomplished by hand swabbing with a cotton swab. It is generally difficult to get into the tight corner areas of the incubating chamber and surrounding area. Thus, the present invention provides means whereby the incubating chamber assembly 12 may be easily and quickly removed from the base section 14 and the motor assembly 16 be removed from the incubator chamber assembly 12. The incubator chamber assembly 12 can then be placed directly in an autoclave or steam sterilize for sterilization. Since the incubating chamber assembly 12 can be thoroughly disinfected this minimizes any chance of later contamination or a potential health hazard to users of the apparatus.

It is to be understood that various modifications can be made without the parting from the scope of the present invention. For example, the support plate may be designed to use other test specimens other than test tubes. For example, the support plate can be designed to hold titrater plates.

We claim:

1. An apparatus for incubating a biological test specimen comprising:
   a base section having drive means therein for providing a rotating motion;
   an autoclaveable incubating chamber, said incubating chamber having a shaker plate mounted therein for supporting a container having a biological test specimen, connecting means for connecting said shaker plate to said drive means in said base section, and blower means for producing an air flow within the incubating chamber;
   blower drive means for driving said blower means in said incubating chamber, said blower drive means being detachably mounted to said incubator chamber;
   means for quickly connecting or disconnecting said autoclaveable incubating chamber from said base section including coupling means for quickly connecting and disconnecting said drive means in said base section to said connecting means in said autoclaveable incubating chamber;
   means for allowing quick connection and disconnection of said blower drive means from said incubating chamber.

2. An apparatus according to claim 1 wherein a flexible coupling means is provided for aligning said blower drive means with said blower means in said incubating chamber.

3. An apparatus according to claim 2 wherein said flexible coupling means comprises a flexible sleeve having one end which mates with said drive means and another end secured to a shaft connected to said blower means.

4. An apparatus according to claim 1 wherein said base section houses control means for operating and controlling said incubating chamber.

5. An apparatus according to claim 1 wherein said incubating chamber further includes means for controlling the temperature of the environment within said incubating chamber.

* * * * *